United States Patent [19]
Pasquariello

[11] Patent Number: 6,060,025
[45] Date of Patent: May 9, 2000

[54] SYSTEMS AND METHODS FOR CATALYST REACTIVATION

[75] Inventor: David M. Pasquariello, Pawtucket, R.I.

[73] Assignee: EIC Laboratories, Incorporated, Norwood, Mass.

[21] Appl. No.: 08/935,946

[22] Filed: Sep. 23, 1997

[51] Int. Cl.[7] .................................................. G01N 27/16
[52] U.S. Cl. ......................... 422/94; 73/31.05; 204/406; 340/633; 422/95; 422/96; 422/98; 422/105
[58] Field of Search ................................. 422/83, 94, 95, 422/96, 98, 105; 73/23.31, 23.32, 31.05; 340/633; 204/406

[56] References Cited

U.S. PATENT DOCUMENTS

| | | | |
|---|---|---|---|
| 4,111,658 | 9/1978 | Firth et al. .............................. | 23/232 |
| 4,123,225 | 10/1978 | Jones et al. ............................. | 422/98 |
| 4,992,384 | 2/1991 | Laurs et al. ............................ | 436/151 |

FOREIGN PATENT DOCUMENTS

| | | | |
|---|---|---|---|
| 269105 A1 | 6/1989 | Germany ................................. | 23/96 |
| 274096 A1 | 6/1989 | Germany ................................. | 27/16 |
| 62/282645 | 12/1987 | Japan ...................................... | 23/96 |
| 2 125554 | 3/1984 | United Kingdom .................... | 27/16 |

*Primary Examiner*—Arlen Soderquist
*Attorney, Agent, or Firm*—Foley, Hoag & Eliot, LLP; Edward J. Kelly; David P. Halstead

[57] ABSTRACT

The invention includes systems and methods which allow reactivation of supported noble metal catalysts. The method involves heating the catalyst in the presence of a gaseous hydrocarbon in the absence of oxidizing agents. Systems of the invention provide for in situ reactivation of catalytic material.

8 Claims, 4 Drawing Sheets

SYSTEMS AND METHODS FOR CATALYST REACTIVATION

FIELD OF THE INVENTION

The invention relates to systems and processes for reactivating poisoned, noble metal-containing catalysts, and more particularly to the reactivation of platinum-containing catalysts used in measuring the concentration of organic gases in air.

BACKGROUND OF THE INVENTION

Scientists and engineers have developed a number of devices that exploit the effects of catalytic reactions. For example, today there are catalytic monitors designed to measure the concentration of organic gases in air, and to detect the existence of hazardous conditions. These monitors can reduce the risk of accident by detecting the presence of explosive gases which can build up or be released at public utilities, propane distributors, fire services, HVAC contractors, landfill operators, steel mills, natural gas buses and other similar locations. These instruments typically include an element that is generally referred to as a pellistor or pelement. A typical pellistor consists of a small ceramic bead cast on a coil of wire, where the wire serves as both a heater and a thermometer. Electronic circuitry determines the resistance of the element and hence he pellistor's temperature rise or the decrease in power required to maintain the pellistor at a constant temperature when exposed to a gas containing a combustible constituent. In effect, the heat of oxidation of the analyte is measured and, through a calibration procedure, related to the quantity of the analyte present in the gas stream. A detailed discussion of pelements and catalytic combustible gas sensors which include such pelements is found in Mosely, P. T. and Tofield, B. C., Solid State Gas Sensors, Adams Hilger Press, Bristol, England (1987).

Pellistor catalysts usually contain palladium, platinum, or a mixture or alloy that includes at least one of these two noble metals. Palladium catalyzes methane combustion in air at a lower temperature than platinum. Platinum, when maintained at a temperature sufficient to combust methane, is less susceptible than palladium to poisoning by sulfur. These characteristics have resulted in palladium sensors being preferred for battery operated equipment where power consumption must be minimized and platinum sensors being preferred for fixed gas detention systems where long life is desirable.

The chemical process catalyzed by the pellistor is the oxidation of an organic gas in air to yield mostly water vapor and carbon dioxide. Although such catalyst systems can work well initially, deposits can build up and remain on the catalyst surface and, in time, decrease the pellistor's sensitivity. Such deposits may form if the gas contains molecules or atoms that are not readily converted to vapors by oxidation. Such molecules or atoms are referred to as catalyst poisons. Commonly encountered poisons for palladium include sulfur-containing organic compounds such as odorants, organohalides, organosilicons, organoleads, and organophosphates. Typically, only organosilicons, organoleads, and organophosphates act to poison pellistors catalyzed by platinum. To address the problem of catalyst poisons, a filter may be incorporated around or on the pellistor. Such pellistors can absorb a finite amount of poison and may have a some-what extended life, but will be poisoned by repeated or high level exposures.

Once poisoned, the catalyst is generally ineffective in detecting the presence of combustible gases. This renders the catalytic device unusable. Consequently, catalytic poisoning is a costly problem as it can destroy the usefulness of expensive catalyst system such as gas detectors, as well as systems for converting conversion or reforming of petroleum feedstocks into other chemical compounds and catalytic air cleaning systems for automotive exhaust gases, which can lose activity due to exposure to the oxidation resistant poisons often contained in engine lubricants. For example, W. H. Preston et al. in the Institution of Mechanical Engineers Papers, Conference on Vehicle Emissions and Their Impact on European Air Quality, 1987–88, has shown a statistical link between the phosphorous content of lubricants and the catalyst performance of automobile air cleaning systems.

Further troubling is that poisoning from metalloids such as boron, silicon, germanium, arsencic, and antimony can resist existing recovery techniques. Specifically, metalloid-poisons form polymeric oxides which are not converted to gases by heating in oxygenated environments. Consequently, although both non-metal and metalloid-containing organic compounds poison noble metal catalysts, the polymeric metalloid oxides cannot be removed by oxidation. Accordingly, there is need for a recovery process that can treat catalysts poisoned by metalloid compounds.

SUMMARY OF THE INVENTION

Accordingly, it is an object of the invention to provide processes that restore catalytic activity for catalysts poisoned by metalloid containing compounds.

It is another object of the invention to provide systems that allow for in situ treatment of pellistors housed within portable or fixed gas detection systems.

Other objects of the invention will be discussed or made apparent from the following description of the invention.

The invention provides methods to reactivate a poisoned noble-metal catalyst, such as a pellistor that includes a noble metal. The catalyst may have been poisoned during field use due to exposure to gases of unknown and uncontrolled composition, or in the laboratory by exposure to air mixed with a compound that includes a metalloid. The methods can consist of contacting the poisoned catalyst with a non-oxidizing, hydrocarbon containing environment under conditions sufficient to achieve a reactivation reaction that restores, in part or in whole, the catalytic activity of the poisoned catalyst. The conditions to achieve this effect can include temperatures that are sufficiently high to achieve the reactivation reaction and, optionally, at temperatures that are sufficiently low enough to avoid, or reduce, sintering effects in the catalyst. In one practice, the catalyst is heated to between about 400° C. and 750° C. The heated catalyst is exposed to a gas stream containing a hydrocarbon such as methane, ethane, or ethylene, either substantially pure or mixed with an inert gas such as nitrogen or argon. In one practice, the hydrocarbon mixture is in concentration of about 14% to 100% hydrocarbon to 86% to 0% inert gas. The gas stream provides, or is part of, a non-oxidizing environment which lacks any substantial amount of oxidizing agent, such as air or oxygen.

More specifically, the processes described herein recovers catalytic activity of a noble metal catalyst by exposing the catalyst to a hydrocarbon-containing, non-oxidizing environment, and controlling the temperature at which the catalyst is exposed to the hydrocarbon-containing, non-oxidizing environment to reactivate substantially portions of the catalyst that have lost activity. The reactivated catalyst can be re-employed within gas detection system, or within another catalytic device.

The term "non-oxidizing environment" as employed herein will be understood to encompass any environment that will not support substantial combustion, and will include any environment that has an oxygen content of approximately zero to two percent, and more preferably less than one percent.

The term "hydrocarbon containing environment" as used herein will be understood to encompass any environment that comprises, in part or in whole, a hydrocarbon compound, including saturated or unsaturated compounds, including any alkanes, alkenes, alkynes, cyclic or ring compounds, branched-chains or derivatives, and for example shall be specifically understood to include methane, ethane, propane, butane and ethylene.

The possible temperature and pressure characteristics of the processes are manifold, and any suitable conditions for achieving the desired reactivation reaction can be employed and are to be understood as within the scope of the invention. Further, the mechanics for achieving the selected environment can vary and can include, for example, heating directly the catalyst, or placing the catalyst within a heated enclosure, or alternatively heating the gas stream.

The systems described herein include systems that provide for the in situ recovery of catalytic activity of pellistors and other catalytic elements employed within gas detector systems, air cleaning systems and other devices. In one embodiment the systems include catalytic gas detectors that have a combustion sensor including a pellistor having a noble metal catalyst. The detectors include a controller capable of operating in a detection mode for monitoring a characteristic of the pellistor, which varies in response to the concentration of a particular gas within a flow of gas. The controller can also operate in a regeneration mode for heating the pellistor to an operating temperature selected to regenerate catalytic activity of the pellistor upon exposure of said pellistor to non-oxidizing, hydrocarbon containing environment. The catalytic gas detector can include a controller that has a regeneration mode for heating the pellistor to between about 400 and 700° C. and preferably approximately 640° C. The controller can include a micro-processor operating responsive to a set of instruction signals including instruction signals for directing the controller to heat the pellistor to a temperature sufficient to reactivate catalytic activity. Optionally, the controller can include a timer for allowing a time period to be selected during which time period the pellistor is maintained at a temperature, or cycled through a set of temperatures, sufficient to reactivate catalytic activity.

In other embodiments, the system can be a stand alone unit that includes a chamber which is dimensioned to receive a pellistor, or a device having a pellistor, and to create an environment suitable for achieving a reactivation reaction that recovers catalytic activity of the pellistor.

Although the systems and methods described herein can be employed for recovering activity of a catalyst having lost activity due to any poisoning material including phosphorous, and silicon, it will also be understood that a further aspect of the invention includes methods and systems for recovering the sensitivity of a catalyst that has been poisoned by a metalloid-containing compound, or any compound upon oxidation that forms a polymeric oxide. The methods can include exposing the catalyst to a non-oxidizing, hydrocarbon containing environment, and controlling the temperature at which the catalyst is exposed to the non-oxidizing, hydrocarbon containing environment to achieve a temperature sufficient to reactivate portions of the catalyst poisoned by the metalloid containing compound.

The term "metalloid containing compound" as used herein will be understood to include any compound comprising an element having properties intermediate between a metal and a non-metal, boron, silicon, germanium, arsenic, tellurium, polonium antimony and any comparable element. Consequently, methods described herein included methods for recovering catalysts that have lost activity from compounds that are deposited as residue on noble metal catalysts, including residue deposited during combustion with oxygen rich gases, and will include catalysts that have lost activity from oxides of metalloid containing compounds that are polymeric and are not readily converted to gases by heating.

The catalysts capable of being treated by the systems and methods described herein include any catalyst comprising, in part or in whole, noble metals including platinum, palladium, silver, iridium, rhodium, ruthenium, and osmiumn and mixtures thereof. These noble metals are typically associated and supported on or with a metal oxide and particularly an oxide of a metal in the left-hand columns of Groups III to VIII of the Periodic Table, including oxides of silicon, aluminum, titanium, zirconium, hafnium, thorium, vanadium, tantalum, chromium, molybdenum, tungsten, uranium, manganese, zinc, colbalt, and nickel. It will be understood that the catalyst can comprise two or more noble metals and/or two or more metal oxides, and that activating or other compounds can be included within the catalyst as well.

The objects and advantages of the systems and methods described herein include the restoration of pellistor catalyst activity without sintering the catalyst or otherwise reducing its active surface area. In particular, the sensitivity of pellistors poisoned by metalloid-containing compounds may be recovered by the methods and systems described herein. Furthermore, some pellistors that lose sensitivity after prolonged periods of use in the field may be restored by a short treatment period including treatment periods of five to ten minutes. Moreover, maintaining appropriate control of the reaction conditions may allow the pellistor to be reactivated without being removed from the analytical instrument in which the pellistor is installed. Consequently, application of the systems and methods disclosed herein may quickly and conveniently restore the lost sensitivity of a pellistor.

Other aspects and embodiments of the invention will be apparent from the following description of certain illustrative embodiments.

BRIEF DESCRIPTION OF DRAWINGS

The following figures depict certain illustrative embodiments of the invention in which like reference numerals refer to like elements. These depicted embodiments are to be understood as illustrative of the invention and not as limiting in any way.

DETAILED DESCRIPTION OF EXEMPLARY EMBODIMENTS

The methods and systems described herein allow for the reactivation of a supported noble metal catalyst by heating the catalyst in the presence of a gaseous hydrocarbon and in the absence of a significant amount of any oxidizing agents that would interfere with the reactivation of the catalyst.

In one aspect, the methods described herein recover catalytic activity of a noble metal catalyst by exposing the catalyst to a hydrocarbon-containing, non-oxidizing environment. The temperature of exposure, and optionally the pressure at which the environment contacts the catalyst, is controlled to provide for conditions such that a reactivation reaction takes place which reactivates some or all portions of the catalyst that have lost activity to a point that allows for re-use of the catalyst. This reactivated catalyst can be re-used within a gas detecting system, thus achieving efficiencies over existing systems.

Figure 1:
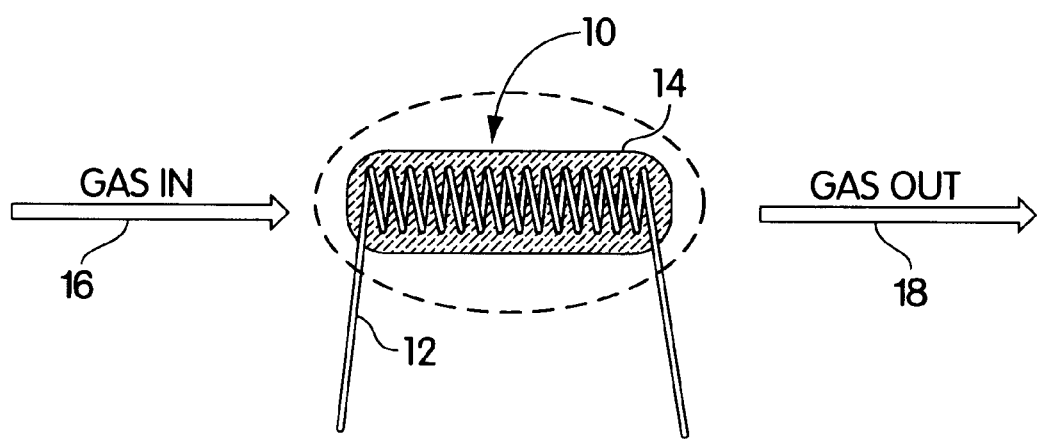
FIG. 1 is a schematic representation of an apparatus in which a hydrocarbon-containing gas is passed across a noble-metal pellistor.

FIG. 1 depicts generally a process for restoring the catalytic activity of a pellistor. Specifically, FIG. 1 depicts a pellistor 10 with a Pt-catalyzed ceramic bead 14 cast on a coil 12 of platinum wire. A gas stream 16 flows toward the pellistor 10 and an exhaust stream 18 flows from the pellistor 10. The gaseous stream 16 is hydrocarbon-containing mixture that lacks any substantial oxygen content. The depicted pellistor 10 is approximately 0.5 to 5 millimeters in diameter and approximately 0.5 to 5 millimeters in length. As will be understood by those of skill in the art, the depicted pellistor 10 is in a poisoned condition, such that catalytic activity has been reduced or eliminated.

In the recovery process depicted by FIG. 1, the poisoned pellistor 10 is heated by passing an electrical current through the wire 12 to raise the pellistor 10 to a temperature of between about 400 and 750° C. The gas stream 16 passes over the heated pellistor 10 to thereby place the pellistor 10 within a hydrocarbon containing, non-oxidizing environment. In one practice, the gas stream 16 comprises substantially pure methane and has an oxygen content of less than one percent or 10,000 parts per million. The poisoned pellistor 10 is maintained within the gas stream 16 for a time period, which for example may be a time period previously determined empirically to restore substantially the catalytic activity of a poisoned pellistor 10. In one practice, the pellistor 10 is maintained within the gas stream for between two and ten minutes. After the predetermined time period, the gas stream 16 can be turned off and the sensitivity of the pellistor 10 can be tested by any suitable technique to determine the success of the recovery process.

The process being practiced in FIG. 1 allows for the in situ recovery of catalytic activity for pellistors, or other catalytic devices. To that end, systems, such as the system 20 depicted in FIG. 2, can include a regeneration mode that implements the recovery process and allows for the re-use of previously poisoned catalyst material.

Figure 2:
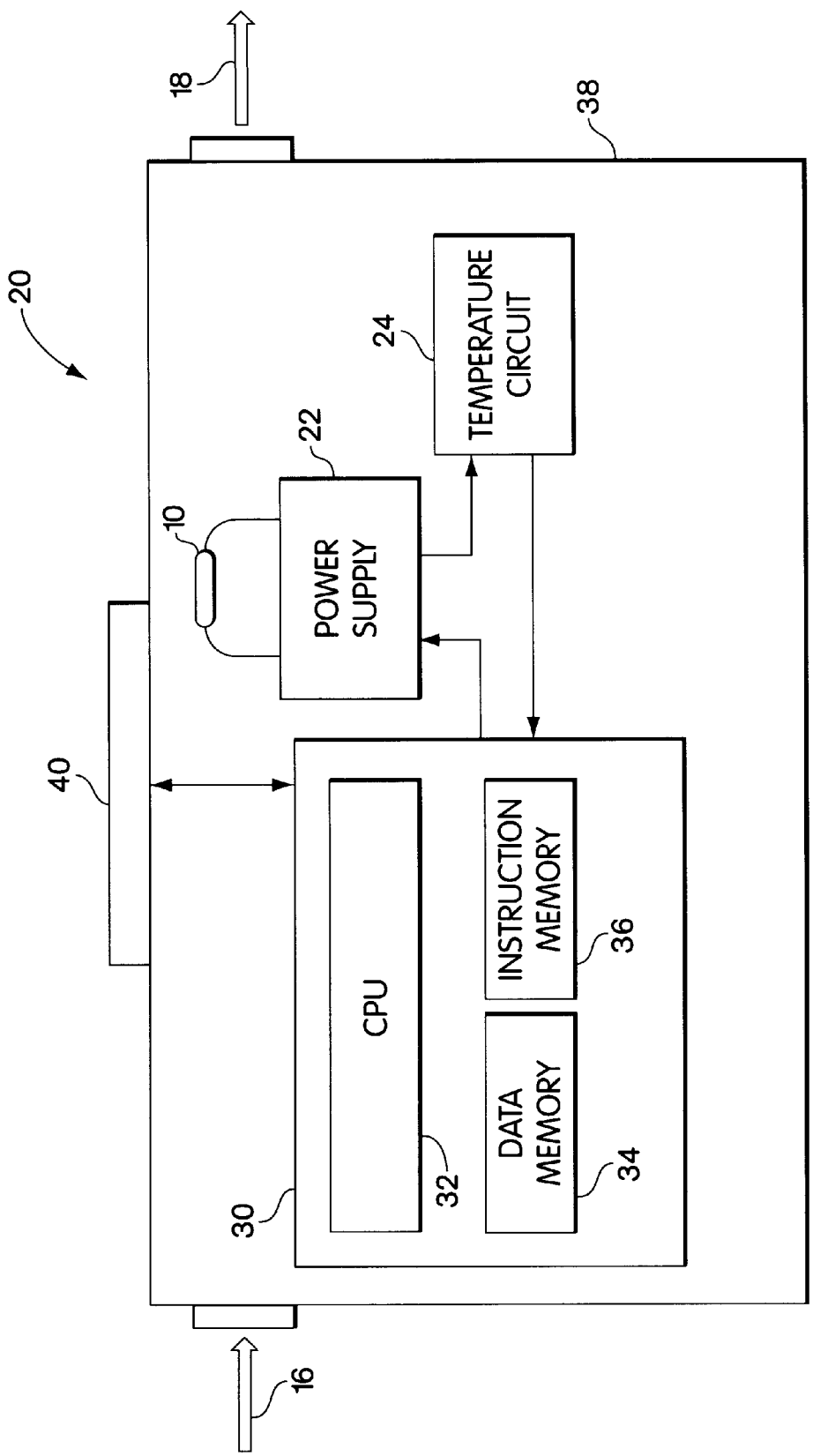
FIG. 2 is a schematic representation of an apparatus for reactivating a pellistor that has been desensitized.

Specifically, FIG. 2 illustrates a system 20 that includes a pellistor 10, an intake port for receiving the flow of gas 16, and exhaust port for venting the flow gas 18, a power supply 22, a temperature circuit 24, a control circuit 30 and a user interface 40. The depicted system 20 can operate in a detection mode and in a regeneration mode. In the detection mode, the system 20 detects the presence or the concentration of certain gases. In the regeneration mode, the system 20 operates to recover in situ any lost activity of the pellistor 10 to allow for re-use or continued use of the pellistor 10.

As is generally known, pellistors of the type depicted in FIGS. 1 and 2 can catalyze the combustion of an organic vapor in the gas stream 16. Typically, the sensitivity of the pellistor 10 is evaluated by measuring the difference in power needed to maintain the pellistor at a predetermined temperature when the gas stream 16 is changed from one containing ambient air to one containing air and methane in which the methane concentration is 2.5% (by volume). As an absolute measure, sensitivity can be reported as mW per percent methane (% $CH_4$), and can depend on the size of the pellistor and therefore the amount of catalyst. In any event, information about the response of the pellistor can be collected and this information measured values can be stored in the control unit 30, such as in a look-up table, or set of equations. Once the sensitivity of the pellistor 10 is measured, the pellistor 10 can be employed within a gas detector to determine the concentration of methane.

When the system 20 operates in a detection mode for detecting the presence and/or concentration of certain gases, the platinum element serves two purposes within the pellistor 10; heating the bead electrically to its operating temperature, typically about 500° C., and detecting the rate of oxidation of the combustible gas. The depicted power supply 22 acts, typically by passing a current through the wire coil, to heat the pellistor 10 to a selected operating temperature. Optionally, the power supply 22 can heat the pellistor to one selected operating temperature which is held constant by the feedback system formed form the power supply 22, the temperature circuit 24 and the controller 30, or can vary the pellistor temperature, such as by cycling the temperature over two or more temperatures during a selected time period, or otherwise varying the temperature.

The rate of oxidation of the combustible gas may be measured in terms of the variation in resistance of the platinum element relative to a reference resistance. The two resistances are generally part of measurement circuit such as a Wheatstone bridge circuit, which can be incorporated as part of the temperature circuit 24. The output or the voltage developed across the circuit when a combustible gas is present provides a measure of the concentration of the combustible gas. The reference resistor generally comprises a compensating, nonactive pellistor having chemical and physical characteristic matched as closely as possible with the pellistor carrying the catalyst. In this way, the temperature circuit 24 can make a determination of the temperature of the pellistor 10.

The temperature measure can be transmitted to the controller 30 which can determine from the temperature the concentration of gas being analyzed, and the controller can display the measured concentration to a user through the interface 40.

Typically, the active pellistor and the compensating pellistor are deployed within an explosion-proof housing, such as housing 38 and are separated from the surrounding environment by a porous metal frit (not shown in FIG. 2). The porous metal frit allows ambient gases to pass into the housing 38 but prevents the "flashback" of flames into the surrounding environment. Such catalytic gas sensors are usually mounted in instruments which, in some cases, are portable and, therefore, carry their own power supply. It is, therefore, desirable to minimize the power consumption of a catalytic gas sensor.

The system 20 can also operated in a regeneration mode. To that end, the depicted system 20 includes a controller 30 that can include a CPU 32, a data memory 34 and an instruction memory 36. Optionally, the CPU 32, data memory 34 and the instruction memory 34 can be incorporated, in part or in whole, into a micro-controller unit, such as the INTEL 8051 series micro-controller. In this embodiment, a computer program can be stored as a set of instruction signals within the instruction memory 36, and the CPU 32 can operate responsive to these instruction signals to regenerate the pellistor 10.

In one such embodiment, the user can run a sensitivity check by connecting the system 20 to a source of gas having a known concentration of methane and running the system 20 in detection mode to determine if the pellistor is capable of correctly reporting the concentration. If not, the user can connect the intake port of the system 20 to a source of hydrocarbon containing gas, having less than two percent oxygen content. The user can then, through interface 40, activate the regeneration mode of system 20. The controller 30 can respond to the instructions in memory 36 to heat the pellistor 10 to a selected temperature, such as a temperature between 400 and 750° C. The controller 30 can then operate as a timer to maintain the pellistor 10 at this temperature for a selected period of time. In a subsequent operation, the controller 30 can then indicate to the user that the pellistor 10 is ready for use, or ready to be checked for increased sensitivity by a process as described above. If sensitivity is recovered, the system 20 can again be operated in detection mode. Alternatively, the system 20 can again be operated in regeneration mode, or optionally the system 20 can indicate through the interface 40 that the pellistor needs to be replaced.

In an alternate embodiment, the systems can include a chamber that has an interior volume sufficiently large to receive a gas detector or other catalytic device, and which includes an intake port that can be coupled to a source of hydrocarbon material. In this way, a stand alone system can be provided into which the catalytic device can be placed, and within which a non-oxidizing, hydrocarbon containing environment can be created by filling the interior volume with a hydrocarbon material so that the environment is substantially lacking any oxygen content, and a non-combustible environment contacts the catalytic device. The catalytic device can be manipulated to allow any catalyst material within the device to be exposed to the environment of the chamber. For example, all appropriate valves can be opened so that a the catalyst material is in fluid communication with the interior of the chamber. The chamber can include a controller, similar to the controller 30, which can heat the interior of the chamber, or the material being placed in the chamber, to reach a selected operating temperature and to maintain this temperature for a selected time. By operating this system, catalytic devices can be restored to operation.

The following examples illustrate further the reactivation process.

EXAMPLE 1

The first example involves a pellistor of the type described above that had a sensitivity of 24 mW/% $CH_4$ until it was exposed to hexamethyldisilazane (HMDS) vapors for 1 minute. After this exposure the sensitivity decreased to 0.2 mW/% $CH_4$. This sensor was exposed to a stream of pure $CH_4$ at different flow rates according to the schedule shown in Table 1, while being heated at a temperature of 640° C. The initial improvement was a sensitivity increase to 4.5 mW/% $CH_4$ after 30 minutes at a $CH_4$ flow rate of 15 $cm^3$ per minute. This treatment was repeated twice, first for 60 minutes, then for 30 minutes. The sensitivity increased to 7.8 mW/% $CH_2$ and 9.6 mW/% $CH_4$ respectively. When the gas flow rate was increased to 200 $cm^3$/minute, the sensitivity improved to 18 mW/% $CH_4$ after approximately one-half hour of treatment. Two additional treatments of 20 minutes and 28 minutes yielded only marginal further improvements to an ultimate sensitivity of 20 mW/% $CH_4$.

TABLE 1

| Time (min.) | Methane Flow Rate ($cm^3$/min.) | Sensor Sensitivity (mW/% $CH_4$) |
|---|---|---|
| 0 | — | 0.2 |
| 30 | 15 | 4.5 |
| 90 | 15 | 7.8 |
| 120 | 15 | 9.6 |
| 154 | 200 | 18 |
| 174 | 200 | 19 |
| 202 | 200 | 20 |
| 232 | 200 | 20 |

EXAMPLE 2

The pellistor of Example 1 was poisoned again by exposure to HMDS vapors for 1 minute, and the sensitivity decreased to 1.1 mW/% $CH_4$. The treatment described in Example 1 was repeated with a $CH_4$ flow rate of 200 $cm^3$/minute and a temperature of 640° C. for 38 minutes, and the sensitivity recovered to 17 mW/% $CH_4$. This example shows that the pellistor activity may be recovered more than once.

EXAMPLE 3

A pellistor similar to the one of Example 1 had a sensitivity of 22 mW/% $CH_4$ until it was exposed to HMDS vapors for 1 minute. At this point the sensitivity decreased to 0.94 mW/% $CH_4$. When the pellistor was heated in $CH_4$, flowing at a rate of 200 $cm^3$/minute, for 30 minutes, at a temperature of 640° C., the sensitivity increased to 10 mW/% $CH_4$. An additional 30 minute treatment under the same conditions raised the sensitivity to 14 mW/% $CH_4$.

EXAMPLE 4

A pellistor similar to the one of Example 1 had a sensitivity of 18 mW/% $CH_4$, which decreased to 0.26 mW/% $CH_4$ when it was exposed for one minute to the vapors emitted by an uncured commercial silicone sealant containing dimethyl siloxane and methyltrimethoxysiliane. The pellistor was heated in $CH_4$, flowing at a rate of 200 $cm^3$/minute, at a temperature of 640° C., for 30 minutes and the sensitivity increased to 12 mW/% $CH_4$. The sensitivity increased to 14 mW/% $CH_4$ when this treatment was repeated for an additional 30 minute period.

EXAMPLE 5

A pellistor similar to the one of Example 1 had a sensitivity of 20 mW/% $CH_4$ until it was exposed to HMDS vapor for 1 minute, which caused the sensitivity to decrease to 0.9 mW/% $CH_4$. Exposure of the heated filament to flowing (200 $cm^3$/minute) ethylene gas for 15 minutes, at a temperature of 640° C., increased the sensitivity to 17 mW/% $CH_4$.

EXAMPLE 6

Figure 3:
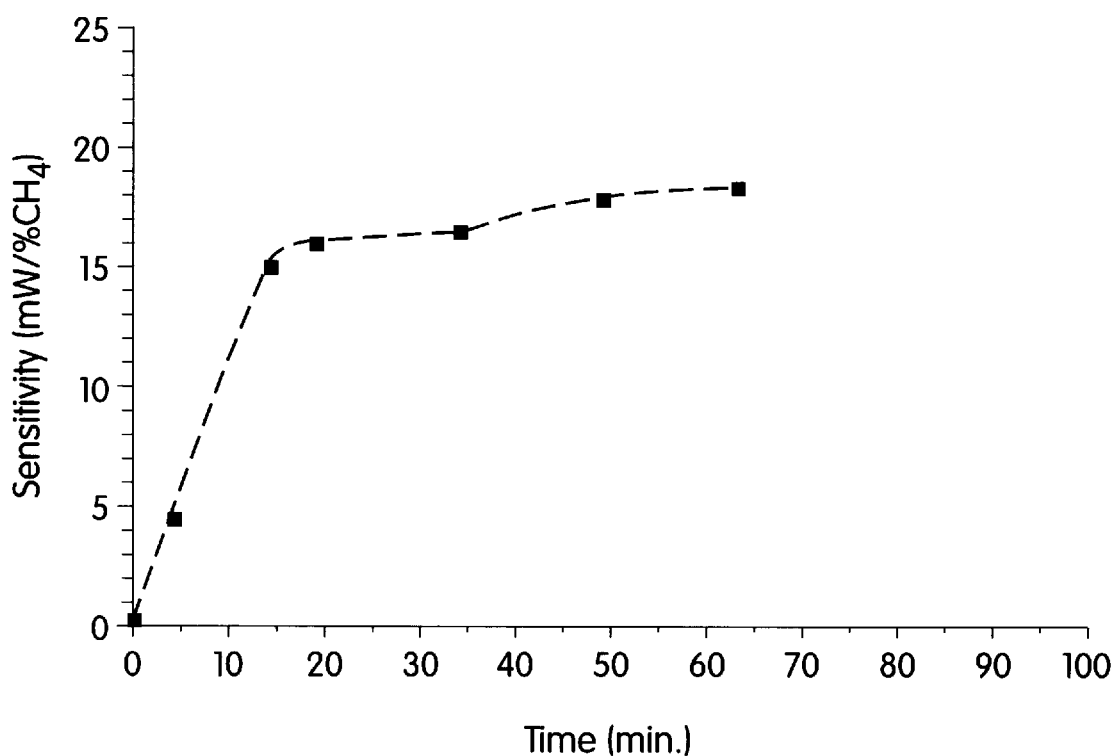
FIG. 3 is a graph that illustrates the recovery of pellistor sensitivity for a pellistor desensitized during field use.

A pellistor similar to the one of Example 1 was recovered from field use after its sensitivity decayed from an initial value of 20.8 mW/% $CH_4$ to 0.26 mW/% $CH_4$. The sensitivity of the filament increased as it was heated to a temperature of 640° C. and exposed to pure $CH_4$ gas at a flow rate 200 $cm^3$/minute. The progressive increase in sensitivity as a function of treatment time is shown in FIG. 3. After 14 minutes of treatment the sensitivity was 15 mW/% $CH_4$ or 72% of its original value. The sensitivity was restored to 18.4 mW/% $CH_4$ or 88.5% of its original value after approximately one hour of treatment.

EXAMPLE 7

A pellistor similar to the one of Example 1 was recovered from field use after its sensitivity decayed from an initial value of 24 mW/% $CH_4$ to 11.7 mW/% $CH_4$. The sensitivity of the filament increased as it was heated to a temperature of 640° C. and exposed to pure $CH_4$ gas at a flow rate of 300 cm³/minute, so that after thirty minutes of treatment the sensitivity was 19.5 mW/% $CH_4$, or 81% of its initial value. The progressive improvement in sensitivity as a result of treatment is shown in Table 2.

TABLE 2

| Time (min.) | Methane Flow Rate (cm³/min.) | Sensor Sensitivity (mW/% $CH_4$) |
|---|---|---|
| 0 | — | 8.4 |
| 10 | 300 | 14.5 |
| 20 | 300 | 16.5 |
| 30 | 300 | 19.5 |
| 40 | 300 | 19.6 |

EXAMPLE 8

A pellistor similar to the one of Example 1 was received from the field after its sensitivity had decayed from 22.8 mW/% $CH_4$ to 8.4 mW/% $CH_4$. The $CH_4$ flow rate of 300 cm³/minute used in Example 1 was reduced in the present example first to 140 cm³/minute, then to 100 cm³/minute. After exposure of the hot filament to 1.8 L of $CH_4$ as detailed in Table 3, the sensitivity increased to 15.1 mW/% $CH_4$. Two more treatments increased the sensitivity first to 17.8 mW/% $CH_4$, then to 18.3 mW/% $CH_4$, so that after 40 minutes of treatment, the sensitivity recovered to 80% of the value obtained when the pellistor was new.

TABLE 3

| Time (min.) | Methane Flow Rate (cm³/min.) | Sensor Sensitivity (mW/% $CH_4$) |
|---|---|---|
| 0 | — | 8.4 |
| 13 | 140 | 14.5 |
| 23 | 100 | 16.5 |
| 33 | 100 | 19.5 |
| 43 | 100 | 19.6 |

EXAMPLE 9

A pellistor similar to the one in Example 1 was placed in used with a sensitivity of 22.8 mW/% $CH_4$, and received from the field with a sensitivity of 0 mW/% $CH_4$. The filament was heated to a temperature of 640° C. and placed in 14% $CH_4$: 86% $N_2$ flowing at approximately 0.4 L/minute. As a result of this treatment, the sensitivity increased to 4.5 mW/% $CH_4$. Subsequent additional 15 minute treatments used gas flow rates of 0.5 L/minute and 1 L/minute. The sensitivity increased to 14.9 mW/% $CH_4$, and 18 mW/% $CH_4$, respectively, after these treatments.

EXAMPLE 10

A sensor similar to the one in Example 1 was placed in service with a sensitivity of 23.2 mW/% $CH_4$, and was received from the field with a sensitivity of 0 mW/% $CH_4$. The filament was heated to a temperature of 640° C. in a $CH_4$ stream flowing at a rate of 300 cm³/minute for two minutes and the sensitivity increased to 11.7 mW/% $CH_4$. The sensitivity increased to 18.4 mW/% $CH_4$ after ten additional minutes of treatment under the same conditions. Within the first four minutes of treatment the sensitivity increased by a factor of 17; after 14 minutes of treatment the sensitivity increased by a factor of nearly 60. Maximum improvement (factor of 70) occurred after one hour of treatment.

EXAMPLE 11

Figure 4:
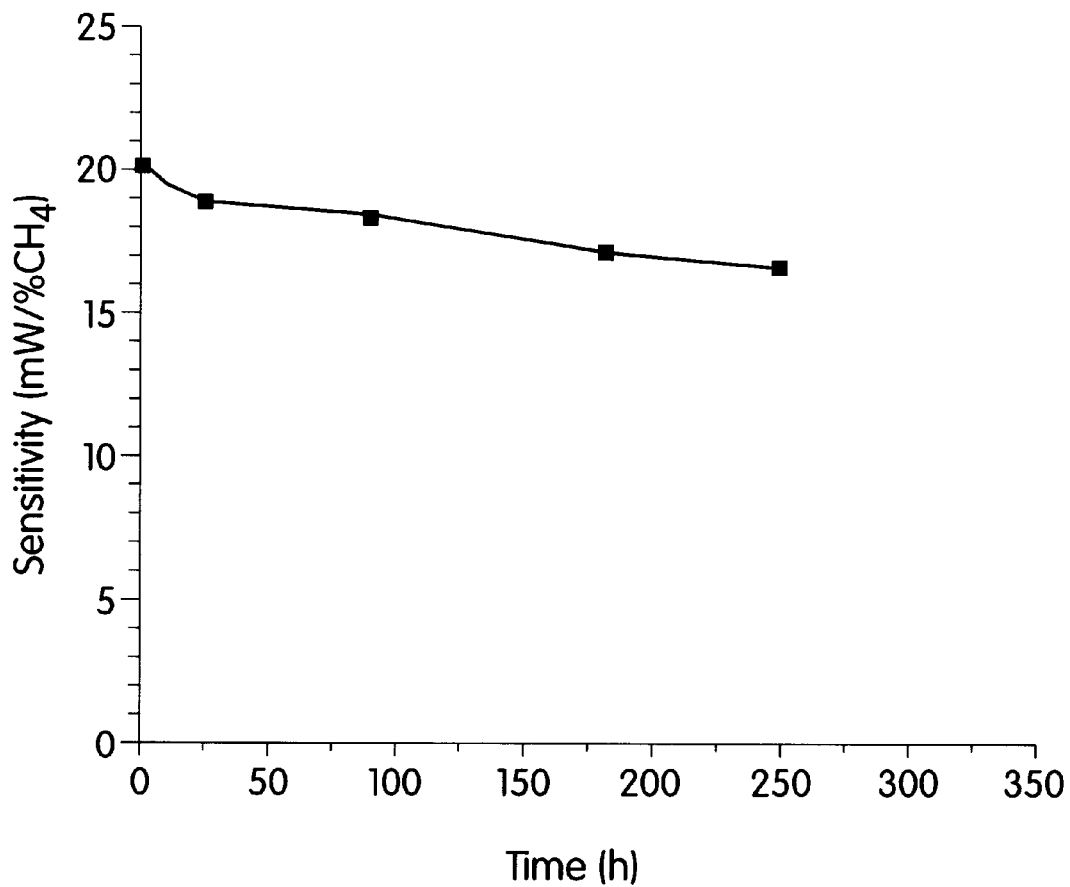
FIG. 4 is a graph that illustrates the performance of a pellistor that has been restored by application of a procedure according to the invention.

The recovered sensor from Example 10 was run in air continuously with periodic interruptions to test the sensitivity. FIG. 4 shows that this recovered sensor retained 83% of its sensitivity after approximately 250 hours of continuous testing.

EXAMPLE 12

A sensor similar to the one in Example 1 but catalyzed with palladium rather than platinum had a sensitivity of 21.2 mW/% $CH_4$ until it was exposed to HMDS vapors for one minute. After this exposure, the sensitivity decreased to 3.1 mW/% $CH_4$. This sensor was exposed to a stream of pure $CH_4$ at a flow rate of 300 cm³/minute while being heated at a temperature of 640° C. After five minutes of such treatment, the sensitivity increased to 14.0 mW/% $CH_4$.

The process described herein can be employed to reactivate pellistors that have lost sensitivity after laboratory experiments in which they are poisoned by organic compounds containing silicon, or after use in the field where they are exposed to gases of unknown composition. The processes may recover sufficient sensitivity to allow reuse of a pellistor that has been poisoned by exposure to a stream of oxygen-free gaseous hydrocarbons such as methane, ethane, or ethylene.

While the invention has been disclosed in connection with certain exemplary embodiments and practices shown and described in detail herein, various modifications and improvements thereon will be readily apparent to those skilled in the art. For example, the length of the exposure period could be varied and the temperature of the process could be increased. Alternatively, a liquid or solid form of hydrocarbon-containing material, or a chemical wish, could be used instead of a gas, or other aromatics could be used instead of hydrocarbon. A filament other than platinum may be used so that the heating process can be performed and controlled at other desired temperatures. Other reaction conditions can be found and selected, and for example can include other temperature ranges for reaction conditions that take place with different chamber pressures for hydrocarbon containing environment. Such temperature and pressure ranges can be selected to achieve improved reactions or commercially useful reaction times and conditions. Accordingly, the spirit and scope of the present invention is to be limited only by the following claims.

I claim:

1. A catalytic gas detector, comprising
   a combustion sensor including a pellistor having a noble metal catalyst,
   a source of non-oxidizing hydrocarbon-containing gas coupled to said combustion sensor, and
   a controller coupled to said combustion sensor, wherein in a detection mode said controller monitors an electrical characteristic of said pellistor, said electrical characteristic varying in response to the concentration of a particular gas within a flow of gas contacting the pellistor, and in a regeneration mode said controller operates to expose the pellistor to a non-oxidizing, hydrocarbon-containing environment and heats said pellistor to a temperature selected to regenerate catalytic activity of said noble metal catalyst diminished by poisoning from a metalloid containing compound.

2. The catalytic detector according to claim 1, wherein the selected temperature is between about 400° C. and about 750° C.

3. The catalytic detector according to claim 2, wherein the selected temperature is about 640° C.

4. The catalytic detector according to claim 1, wherein said controller includes a micro-processor unit operating responsive to a set of instruction signals including instruction signals fore directing said controller to heat said pellistor to the selected temperature.

5. The catalytic detector according to claim 1, further comprising a timer for regulating a time period during which the pellistor is heated to the selected temperature.

6. Apparatus for recovering sensitivity of a catalytic gas detector having a noble metal catalyst poisoned by a metalloid containing compound, comprising a chamber dimensioned for receiving the catalytic gas detector having an intake port couple to a source of hydrocarbon-containing gas having an oxygen content of less than about two percent, to thereby provide within said chamber a non-oxidizing, hydrocarbon-containing environment, and a controller coupled to said chamber, wherein said controller provides said chamber with the non-oxidizing, hydrocarbon-containing gas and heats said catalytic device to a temperature selected to regenerate catalytic activity of said noble metal catalyst diminished by poisoning from the metalloid containing compound.

7. Apparatus according to claim 6, wherein said chamber includes an exhaust port for allowing said hydrocarbon-containing gas to flow through said chamber.

8. Apparatus according to claim 6, wherein said chamber is dimensionally adapted to receive a volume of the hydrocarbon-containing gas sufficient to provide within said chamber said non-oxidizing, hydrocarbon-containing environment, and to thereby allow for recovery of catalytic activity.

* * * * *